(12) United States Patent
Thomson

(10) Patent No.: US 7,838,835 B2
(45) Date of Patent: Nov. 23, 2010

(54) DEVELOPMENT OF DISPOSABLE/SEALABLE CAPS FOR SPECTROSCOPIC PROBES

(75) Inventor: Alasdair Iain Thomson, Hull (GB)

(73) Assignee: BP Oil International Limted, Middlesex (JP)

( * ) Notice: Subject to any disclaimer, the term of this patent is extended or adjusted under 35 U.S.C. 154(b) by 412 days.

(21) Appl. No.: 11/922,139

(22) PCT Filed: Jun. 13, 2006

(86) PCT No.: PCT/GB2006/002162

§ 371 (c)(1),
(2), (4) Date: Dec. 13, 2007

(87) PCT Pub. No.: WO2006/136787

PCT Pub. Date: Dec. 28, 2006

(65) Prior Publication Data

US 2009/0310124 A1    Dec. 17, 2009

(30) Foreign Application Priority Data

Jun. 20, 2005    (EP) .................................. 05253810

(51) Int. Cl.
*G01J 5/04* (2006.01)
*G01J 3/00* (2006.01)
*G01N 21/01* (2006.01)
*G01N 21/84* (2006.01)

(52) U.S. Cl. .............................. 250/339.07; 250/339.12; 250/576; 356/440; 356/436; 356/326; 356/246

(58) Field of Classification Search ................. 250/576, 250/573, 339.07, 339.12; 356/440, 436, 356/326, 246
See application file for complete search history.

(56) References Cited

U.S. PATENT DOCUMENTS

| | | | | |
|---|---|---|---|---|
| 5,077,481 A | * | 12/1991 | Hoult | 250/576 |
| 5,335,067 A | * | 8/1994 | Prather et al. | 356/436 |
| 5,381,237 A | * | 1/1995 | Sela | 356/436 |
| 5,754,722 A | * | 5/1998 | Melling | 385/115 |
| 7,683,327 B2 | * | 3/2010 | Thomson | 250/339.11 |
| 2004/0086215 A1 | * | 5/2004 | Salerno et al. | 385/12 |

FOREIGN PATENT DOCUMENTS

JP    62-242839    10/1987
JP    2002-194351    7/2002

OTHER PUBLICATIONS

PCT International Search Report mailed Aug. 21, 2006.
PCT Written Opinion of the International Searching Authority dated Aug. 21, 2006.

* cited by examiner

*Primary Examiner*—David P Porta
*Assistant Examiner*—Yara B Green
(74) *Attorney, Agent, or Firm*—Nixon & Vanderhye

(57) ABSTRACT

The present invention relates to a sealable cell for measuring a liquid sample comprising a spectroscopic probe and a removable cap that can accommodate at least the head of the probe, wherein the internal wall of the cap comprises one or more grooves which are disposed so as to allow a liquid sample to enter the head of the probe and air to escape from the head of the probe to enable improved spectra to be obtained.

16 Claims, 3 Drawing Sheets

DEVELOPMENT OF DISPOSABLE/SEALABLE CAPS FOR SPECTROSCOPIC PROBES

This application is the U.S. national phase of International Application No. PCT/GB2006/002162 filed 13 Jun. 2006, which designated the U.S. and claims priority to EP 05253810.5 filed 20 Jun. 2005, the entire contents of each of which are hereby incorporated by reference.

The present invention relates to the development of disposable/sealable caps for spectroscopic probes for the measuring the electromagnetic spectrum, particularly the near infrared spectrum, of liquid samples.

NIR spectroscopy is a well-known spectroscopic technique that looks specifically at the absorptions of infra-red radiation with frequencies of above 4000 cm$^{-1}$. NIR spectroscopy can be used to measure the intensity of the overtones of the molecular vibrations in a molecule, containing carbon-hydrogen, oxygen-hydrogen, and nitrogen-hydrogen bonds. The carbon-hydrogen (C—H) absorption bands are typically useful for mixtures of organic compounds. Different types of C—H bonds, e.g., aromatic, aliphatic, and olefinic hydrocarbons, absorb light at different characteristic frequencies. The magnitude of the absorption band in the spectra is proportional to the number of C—H bonds present in the sample. Hence, NIR spectroscopy is often used to obtain a fingerprint of a sample and by empirically correlating the said fingerprint the intrinsic properties of the sample may also be known.

The NIR region between 780 nanometers (nm) and 2500 nm (12800 to 4000 cm$^{-1}$) is an area of great interest and contains a large amount of molecular information in the form of combinations and overtones from polyatomic vibrations. Mathematical techniques are essential to utilize this information and to calculate the desired properties. U.S. Pat. Nos. 5,490,085; 5,452,232; and 5,475,612, for example, describe the use of NIR for determining octane number, yields and/or properties of a product of a chemical process or separation process from analysis on the feeds to that process, and yields and/or properties of a product of a blending operation again from analysis on the feed thereto.

NIR spectroscopy can be applied to crude oils and other hydrocarbon refinery streams. WO 00/039561 and WO 03/048759, for example, both describe application of NIR to crude oil analysis.

The analysis of crude oil samples, for example, can be performed by generating chemometric models correlating spectral data from "standard" (i.e. characterised) crude oil samples with the known properties of the samples, and subsequently applying said models to the spectra of "unknown" samples to characterise the properties thereof. "Chemometrics" is the application of mathematical and statistical techniques to the analysis of complex data, and hence "chemometric model" means a model generated from application of such techniques in correlating the spectral data from a sample with properties of the sample and cell pathlength. The chemometric model determines the relationship between the spectral data and the cell pathlength as it would for the chemical and/or physical properties (via eigenvectors of a covariance matrix).

The generation of the chemometric model can be done using any one of a variety of techniques/mathematical and statistical techniques, as described, for example, in Principal Component Analysis, I. T. Jolliffe, Springer-Verlag, New York, 1986; D. M. Halland and E. V. Thomas, Anal. Chem., 60, 1202 (1988) or K. R. Beebe and B. R. Kowalski, Anal. Chem., 59, 1007A (1987).

The analysis of samples such as crude oils is typically done using a transmission cell into which the sample is introduced. The cells typically have a relatively short pathlength so that a reasonable signal is transmitted through the cell. However, such cells require cleaning when used with substances such as crude oils. This is by no means a trivial task when using fixed (solid) cells, so demountable cells are the preferred option. Demountable cells may be disassembled, cleaned and then reassembled again for re-use.

The problem faced with demountable cells, however, is that during the disassembly and reassembly the pathlength of the cell may change. With cells that have a relatively short pathlength, even small changes in the pathlength can have significant effects on the spectra obtained. For example where spectral data from "standard" (i.e. characterised) crude oil samples is being measured for generation of a suitable chemometric model correlating various properties of the crude oil samples with the spectral data, the variations in cell pathlength can have significant detrimental effects on the model obtained.

By convention there are three main types of spectroscopic probes that can be utilised within the aforementioned NIR transmission cells; the transflection (transmission reflection) probe, ATR (attenuated total reflectance probe) and the DRIFTS (Diffuse reflectance infrared Fourier transform spectroscopy) probe. The transflection probe comprises an NIR probe containing two optical fibres, normally silica, such that light is passed down one fibre which is then projected through a lens/window at the lower end of the probe and reflected—via a mirror—back through the window into the return fibre. A gap between the window and the mirror—the sample support—allows the sample of interest to enter into the light beam and thus an absorption spectrum is obtained.

The DRIFTS probe is similar to the former however there is no mirror present to reflect the light back into the return fibre and as such is normally used to collect spectra from solid samples.

Unfortunately, whilst assembling the transmission cell in order to characterise a sample, as air is present in the optical path, it generates significant inaccuracies in the data obtained.

The applicants believe that the present invention discloses an apparatus that firstly allows the liquid sample to be sealed within the cell and advantageously maintained at elevated temperatures and pressures and secondly allows the spectroscopic measurement of the liquid samples to be done with a higher degree of accuracy by removing air from the optical path and/or by preventing air from entering into the optical path.

Thus, the present invention relates to a sealable cell for measuring the spectrum of a liquid sample comprising a spectroscopic probe, which spectroscopic probe has a head comprising at least one optical fibre, a window, a reflecting mirror, a sample support located between the window and the mirror comprising an entrance passage and an exit passage; and which sealable cell also comprises a removable cap that accommodates at least the head of the probe such that the distance between the internal wall of the removable cap and the head of the spectroscopic probe is less than 0.4 mm; characterised in that the internal wall of the removable cap comprises one or more grooves disposed such that, when the spectroscopic probe is inserted into the cap, the entrance and exit passages of the sample support coincide with the one or more grooves and provide a path for fluid to flow from the base of the cap, and into and through the sample support.

According to a preferred embodiment of the present invention the spectroscopic probe comprises a head, into which two silica optical fibres lead, and which head also comprises windows, a reflecting mirror, a sample support (located between the window and the mirror), a passage for entering the sample support and a passage for exiting the sample support. The said passages for entering and exiting the sample support are preferably interconnecting and located opposite to each other on the head of the spectroscopic probe. The spectroscopic probe can be made of any appropriate material, preferably metal, more preferably stainless steel.

The probe is preferably a cylindrical probe, having an outer head diameter D. The cap preferably has a circular cross section with an internal diameter D' of less than (D+0.4 mm). D is preferably more than 1.5 mm and less than 30 mm; more preferably more than 6 mm and less than 7 mm; and most preferably more than 6.2 mm and less than 6.6 mm.

The removable cap is adapted to accommodate at least the head of the probe. The distance between the outer wall of the spectroscopic probe and the inner wall of the disposable cap is less than 0.4 mm. In one embodiment of the invention, the removable cap is narrower than the probe, and is preferably up to 0.4 mm narrower than the probe, more preferably up to 0.2 mm narrower. In this embodiment, the cap is made of a material that can stretch and fit over at least the head of the spectroscopic probe.

The internal diameter D' of the removable cap is preferably more than (D−0.4 mm), more preferably more than (D−0.2 mm). The internal diameter D' of the cap is preferably less than (D+0.4 mm), more preferably less than D.

The spectroscopic probe is preferably suitable for use in infrared spectroscopy, more preferably NIR spectroscopy. Preferably the windows surrounding the sample support in the spectroscopic probe may be one of any of the following suitable materials, silica, sapphire or standard salt windows (such as $CaF_2$, $MgF_2$, NaCl, KBr). More preferably the window at the base of the sample support comprises a flat sapphire with a gold mirror attached to the rear.

The removable cap of the spectroscopic probe is shaped so as to accommodate at least the head of the probe, suitably having a cup-shaped longitudinal section. The internal wall of the cap comprises one or more depressions or grooves in the internal wall. The grooves provide a means for a fluid to pass from the base of the removable cap, and into and through the sample support via the entrance and exit passages. The fluid can be a liquid sample and/or a gas, such as air or a volatile component of a liquid sample. Preferably, the grooves are designed so that, on leaving the exit passage, gases and/or any excess liquid sample can leave the cell altogether. This is preferably achieved by ensuring that the groove connecting with the exit passage of the sample support extends to the top of the internal wall of the cap to allow gases or liquids to escape from the cell. This reduces the chances of gas bubbles forming in the sample support which could negatively affect the quality of the spectral data.

The grooves preferably have a cross-sectional area of at least 0.1 $mm^2$ so as not to restrict the flow of liquids, particularly viscous liquids, to too great an extent. This is because a slower flow of liquid is generally less efficient at removing gases, such as air or volatile components of the sample, from the sample support.

In a preferred embodiment, the cap comprises two grooves on the internal wall, one which connects the base of the cap to the sample support entrance passage, and another which connects the exit passage of the sample support to the top of the cap. Preferably the two said grooves are located opposite to each other on the internal wall of the cap. The one or more grooves may be vertically or helically arranged, preferably vertically, and they may have one of many different shapes and configurations, such as having a U-shaped or V-shaped cross section.

The removable cap can be made of any appropriate material preferably Teflon or a thermoplastic material such as polypropylene or polythene. In a preferred embodiment of the invention, the removable cap is disposable to prevent contamination of subsequently analysed samples, the aforementioned preferred cap materials being convenient in this regard due to their relatively low cost.

The sample is preferably a liquid sample. The sample may be a hydrocarbon sample, e.g. a crude oil or "equivalent" sample. By "equivalent" sample is meant a sample that may be used either in place of or blended with a crude oil in a refinery, such as a synthetic crude, a biocomponent, an intermediate stream, such as a residue, gas oil, vacuum gas oil, naphtha or cracked stock, and blends of one or more of said components. The present invention is especially useful for measuring liquids that contain volatile components.

Other hydrocarbon samples to which the process of the present invention may be applied include fuels, lubricants, polymers (liquid polymers or polymer melts) and petrochemicals which are prone to fouling.

According to an embodiment of the present invention the spectroscopic measurement begins with the liquid sample occupying the base of a cap having two grooves. The spectroscopic probe is then inserted—whilst maintaining contact with the internal walls of the removable cap—vertically down into the base of the removable cap; the said one or more grooves consequently provide a means for air and/or any other gases to escape from the cell, thus preventing any air from being trapped above the sample, as illustrated in FIG. 2.

After insertion of the probe into the removable cap the liquid sample enters into the designated groove of the removable cap and subsequently into the sample support of the probe through the entrance passage. Once the sample support has filled, the excess sample flows through the exit passage of the sample support and into the groove that leads from the exit passage to the top of the internal wall of the removable cap, thus allowing any gases and excess liquid to exit the cell.

According to a preferred embodiment, after the insertion of the spectroscopic probe into the removable cap, the assembled cell is then transferred into an aluminium heating block where the cell is sealed using a suitable press. The whole cell—and hence the sample—is then heated and a spectrum is recorded.

An advantage of the present invention is that the sample may be elevated to high temperatures and pressures without the loss of volatile substances. Suitably, inside the sample support the temperature is in the range 10° C. to 200° C. depending on the sample. For practical purposes a temperature slightly above ambient temperature, for example, in the range 30° C. to 90° C. is most preferred. Temperatures and pressures outside of the stated limits are not excluded; however they do not fall under the preferred embodiments of the present invention.

Prior to the measurement of the sample of interest, the pathlength of the cell may be measured by filling the cell with a standard solution, such as toluene, and measuring the spectrum. Preferably according to the present invention the pathlength is in the range of from 0.5 mm to 10 mm. The pathlength is defined by the distance that electromagnetic radiation travels through the sample before reaching the detector. Thus, where incident radiation passed from one optical fibre, through the sample in the sample support, reflects off the mirror, and passes back through the sample, then the pathlength will be twice the thickness of the portion of the sample located between the one or more optical fibres in the spectroscopic probe and the reflecting mirror.

The invention is further illustrated by the attached figures, in which.

Figure 1:
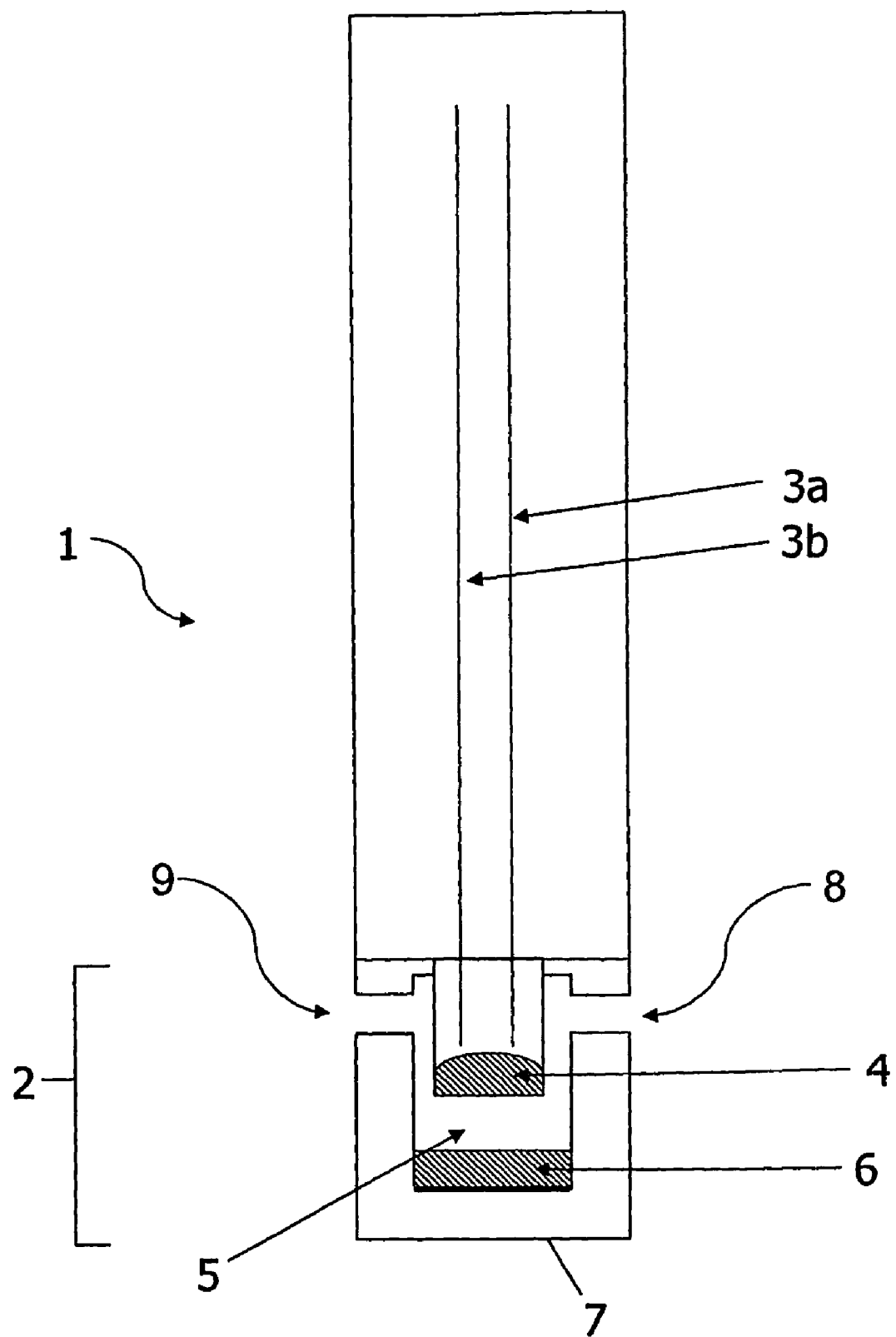
FIG. 1 is a longitudinal section through a spectroscopic probe in accordance with the present invention.

FIG. 1 shows a spectroscopic probe 1 with head 2. NIR radiation is transferred through optical fibres 3a, through a sapphire D-lens 4, where it is focussed onto a sample held in the sample support 5 on top of a sapphire window 6. The radiation passes through the sample and the sapphire window, where it is reflected back through the sample by gold mirror 7 on the base of the sapphire window. The reflected NIR radiation is transmitted to a detector (not shown) via silica optical fibre 3b. Also shown on FIG. 1 are the entrance 8 and exit 9 passages of the sample support.

Figure 2:
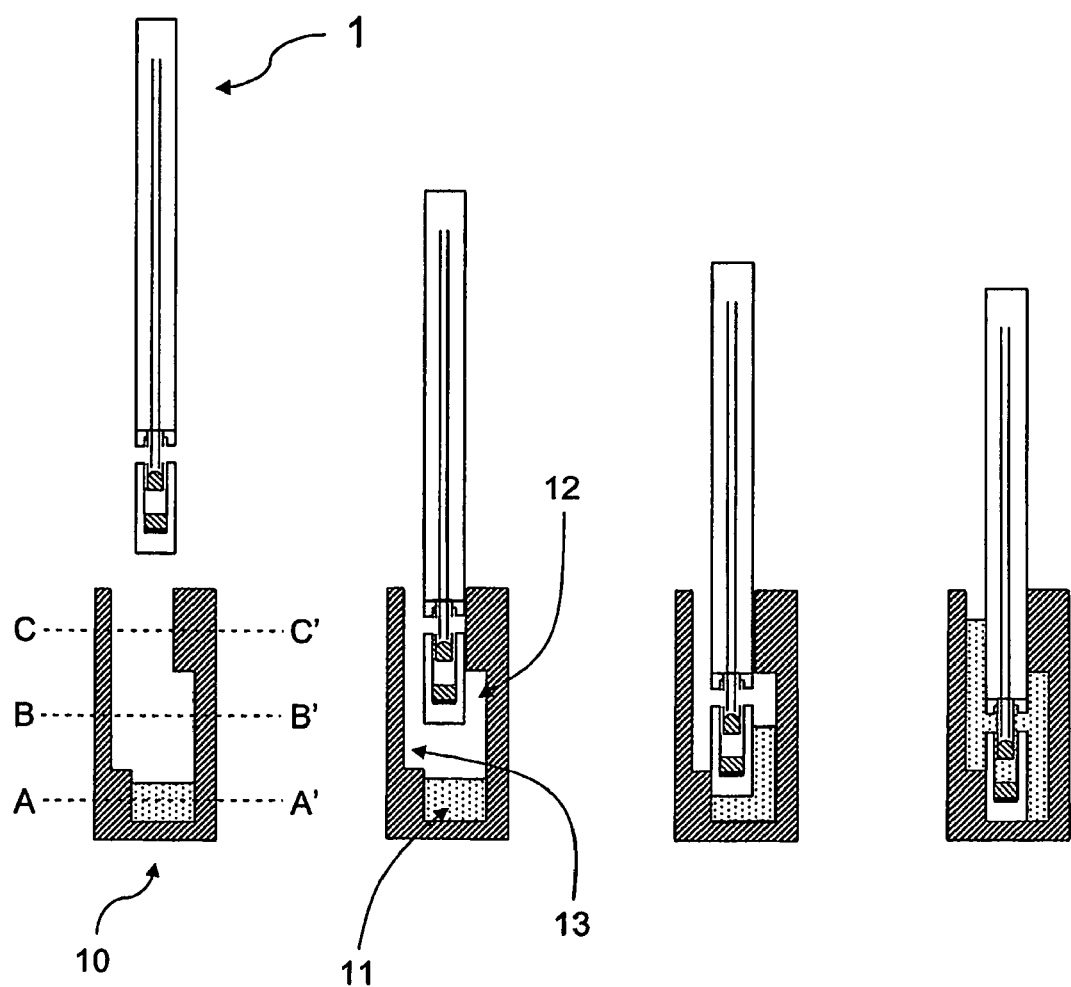
FIG. 2 illustrates a sequence of steps in which a spectroscopic probe is inserted into a removable cap containing a liquid sample.

FIG. 2 illustrates a sequence (from left to right) in which a spectroscopic probe 1 is inserted into a removable cap 10 containing a liquid sample 11. As the probe is inserted, the liquid sample is initially forced up groove 12 on the inner wall of the cap. When the probe is inserted further into the cap, the level of the liquid sample reaches the entrance passage of the sample support of the probe, at which point the liquid sample flows into the sample support, and out through the exit passage into another groove 13, which connects to the top of the inner wall of the cap.

Figure 3:
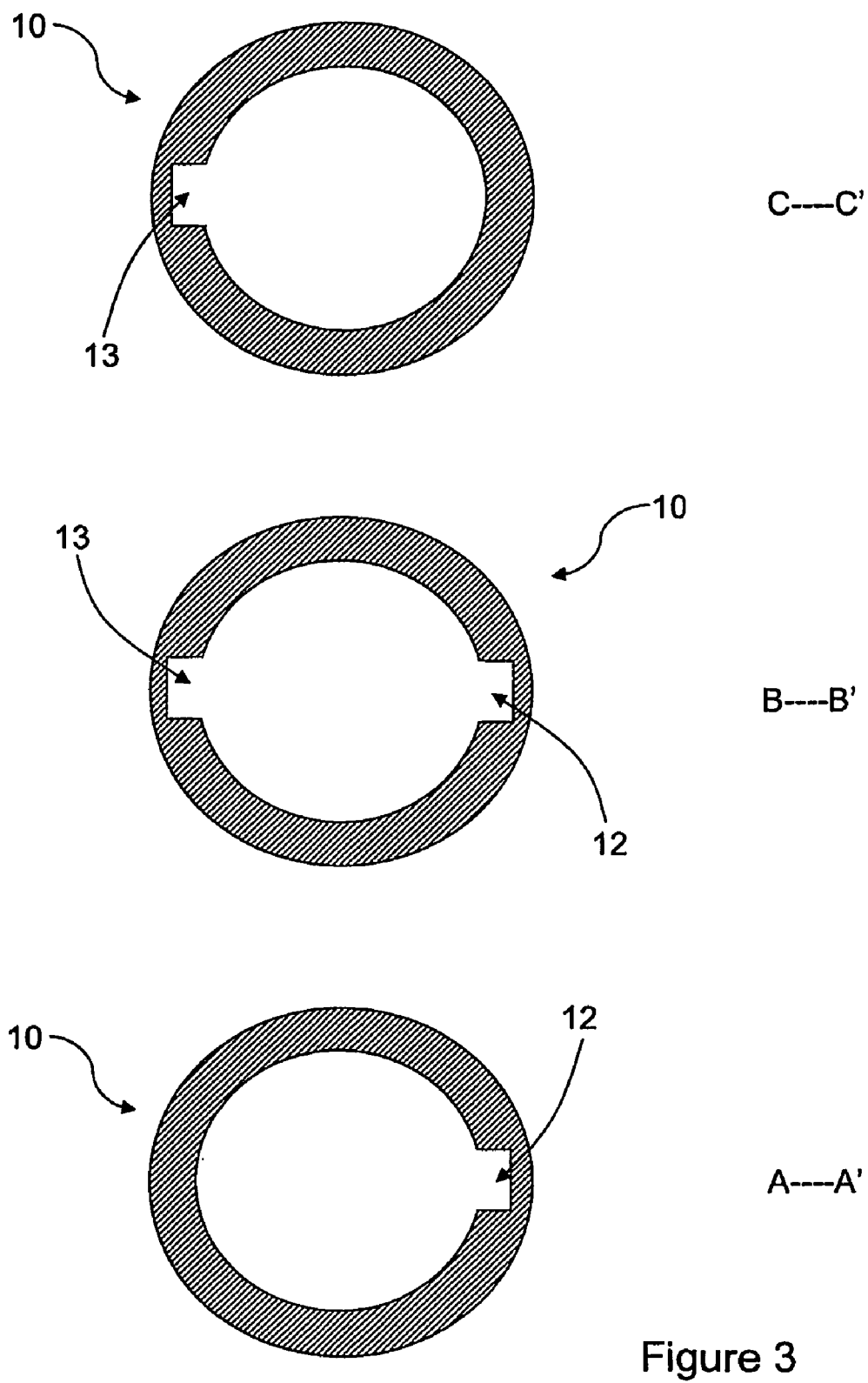
FIG. 3 shows a series of cross-sections through the removable cap illustrated in FIG. 2.

FIG. 3 illustrates cross sections through axes A-A', B-B' and C-C' of the cap 10 as shown in FIG. 2. In the embodiment shown, there are two vertically-disposed grooves on the inner wall of the cap, one of which 12 extends from the base of the cap to a position above the point where the entrance passage of the sample support of the probe lies when the probe is fully inserted. The other groove 13 is located on the opposite side of the inner wall of the cap and extends from a point below the exit passage of the sample support of the probe when fully inserted and up to the top of the cap.

The invention claimed is:

1. A sealable cell for measuring the spectrum of a liquid sample comprising a spectroscopic probe, which spectroscopic probe has a head comprising at least one optical fibre, a window, a reflecting mirror, a sample support located between the window and the mirror comprising an entrance passage and an exit passage; and which sealable cell also comprises a removable cap that accommodates at least the head of the probe such that the distance between the internal wall of the removable cap and the head of the spectroscopic probe is less than 0.4 mm; wherein the internal wall of the removable cap comprises one or more grooves disposed such that, when the spectroscopic probe is inserted into the cap, the entrance and exit passages of the sample support coincide with the one or more grooves and provide a path for fluid to flow from the base of the cap, and into and through the sample support.

2. A sealable cell according to claim 1, wherein the probe and the removable cap are cylindrical, in which the cylindrical probe has a diameter D, and the internal diameter, D', of the removable cap is less than (D+0.4 mm).

3. A sealable cell according to claim 2, wherein the internal diameter D' of the probe cap is cap is more than (D−0.4 mm).

4. A sealable cell according to claim 3, wherein the internal diameter D' of the probe cap is more than (D−0.2 mm).

5. A sealable cell according to claim 2, wherein the internal diameter D' of the probe cap is less or equal to D.

6. A sealable cell as claimed in claim 1, in which the internal wall of the removable cap comprises two grooves, one of which allows air and/or liquid sample to pass from the base of the removable cap to the entrance passage of the sample support, and the other of which allows air and/or liquid sample to leave the sample support via the exit passage and to leave the cell.

7. A sealable cell according to claim 6, wherein the grooves on the internal wall of the cap are arranged such that one groove provides a path from the base of the removable cap to the entrance passage of the sample support, and the other of which provides a path from the exit passage of the sample support to the top of the cap.

8. A sealable cell according to claim 6, wherein the said two grooves are located opposite to each other on the internal wall of the cap.

9. A sealable cell according to claim 1, wherein the entrance and exit passages of the sample support are interconnecting and located opposite to each other on the head of the probe.

10. A sealable cell as claimed in claim 1, in which the cross-sectional area of the one or more grooves is at least 0.1 mm².

11. The sealable cell according to claim 1 wherein the liquid sample contains volatile substances.

12. The sealable cell according to claim 1 wherein the spectroscopic probe performs NIR spectroscopic measurements.

13. The sealable cell according to claim 1 wherein the liquid sample is a hydrocarbon sample.

14. The sealable cell according to claim 13 wherein the hydrocarbon sample is selected from crude oil, samples that can be used either in place of or blended with crude oil in refinery, fuels, lubricants, liquid polymers, polymer melts and petrochemicals which are prone to fouling.

15. The sealable cell according to claim 14 wherein the samples that can be used either in place of or blended with crude oil in a refinery are selected from a synthetic crude, a biocomponent and an intermediate stream.

16. The sealable cell according to claim 15 wherein the intermediate stream is selected from one or more of residue, gas oil, vacuum gas oil, naphtha and cracked stock.

* * * * *